United States Patent
Ueno et al.

(10) Patent No.: US 6,339,088 B1
(45) Date of Patent: Jan. 15, 2002

(54) COMPOSITION FOR TREATMENT OF EXTERNAL SECRETION DISORDERS EXCEPT HYPOLACRIMATION

(75) Inventors: Ryuji Ueno, Montgomery; Ichie Kato, Kawanishi, both of (JP)

(73) Assignee: R-Tech Ueno. Ltd., Osaka-Fu (JP)

(*) Notice: Subject to any disclaimer, the term of this patent is extended or adjusted under 35 U.S.C. 154(b) by 0 days.

(21) Appl. No.: 09/673,563

(22) PCT Filed: Feb. 15, 2000

(86) PCT No.: PCT/JP00/00810

§ 371 Date: Jan. 3, 2001

§ 102(e) Date: Jan. 3, 2001

(87) PCT Pub. No.: WO00/48447

PCT Pub. Date: Aug. 24, 2000

Related U.S. Application Data

(60) Provisional application No. 60/120,725, filed on Feb. 18, 1999.

(51) Int. Cl.$^7$ ............................................. A61K 31/505
(52) U.S. Cl. ....................................... 514/259
(58) Field of Search ........................................ 514/259

(56) References Cited

U.S. PATENT DOCUMENTS 4,734,419 A    3/1988   Masashi et al.

FOREIGN PATENT DOCUMENTS

| EP | 0 301 466 A | 2/1989 |
| EP | 0 331 059 A | 9/1989 |
| WO | 00 01676 a  | 1/2000 |

OTHER PUBLICATIONS

AO S et al: "Effect of instillation of aldose reductase inhibitor FR74366 on diabetic cataract", Investigative Opthalmology And Visual Science, (1991 Nov.) 32 (12) 3078–83, XP000951485.

Kanamaru, Mitsutaka et al, "Aldose reductase inhibitory and uricosuric activities of FK366 in healthy volunteers" J. Clin. Pharmacol. (1993), 33 (11), 1122–31, XP00051478.

Primary Examiner—Rebecca Cook
(74) Attorney, Agent, or Firm—Sughrue Mion, PLLC

(57) ABSTRACT

A composition for treatment of external secretion disorders except hypolacrimation which comprises, as an active ingredient, an aldose reductase inhibitor. The composition is effective in at least one of diseases selected from hyposalivation and dry mouth syndrome.

7 Claims, No Drawings

COMPOSITION FOR TREATMENT OF EXTERNAL SECRETION DISORDERS EXCEPT HYPOLACRIMATION

This is a 371 of PCT/JP00/00810 filed Feb. 13, 2000 which claims priority to Ser. No. 60/120,725 filed Feb. 18, 1999.

TECHNICAL FIELD

This invention relates to a composition for treatment of external secretion disorders except hypolacrimation, and more particularly to a composition for treatment of hyposalivation and a so-called "dry mouth syndrome"

BACKGROUND ART

External secretions are discharges that are discharged directly by way of a glandular cell, or through an excretory duct or the like onto a body surface or into a lumen. One of well-known external secretions is saliva, and the others are secretion from nasal mucous membranes and mucous membranes of a respiratory tract, secretion from a stomach and an intestine, discharges from a vagina, perspiration, etc. Some of diseases resulting from disorder of the above-mentioned external secretion are: dryness of various parts of body such as so-called "dry mouth syndrome" (xerostomia), "dry nose syndrome" (xeromycteria), "dry skin" (xeroderma), "dry vagina syndrome" (symptom of vaginal dryness); and chronic pancreatitis, chronic gastritis, and chronic bronchitis due to depression of external secretion.

It is true that there are a variety of factors that cause disorder of external secretion, some of which still remain unidentified. One of the factors is known as "Sjögren's syndrome", an autoimmune disease. "Sjögren's syndrome" is characterized by a symptom of dryness due to infiltration of phlogocyte onto an acinus of an exocrine gland and around an excretory duct, and destruction and atrophy of the acinus and an epithelial cell of the excretory duct that follows. One of the characteristic symptoms is eye and mouth dryness, as well as dryness of skin, nose, throat, bronchia, vulva, and vagina. Among these, dryness of a respiratory tract may induce infections of the lung, and in a worst case, may cause a serious disorder such as pneumonia that may lead to death. Although disorder of external secretion may cause serious diseases as mentioned above, merely a symptomatic treatment such as artificial hydration has been conducted so far. Therefore, development of a fundamental treatment to improve depressed external secretion humor has been demanded.

One of the diseases resulting from disorder of external secretion which has been a current keen interest in the medical and pharmaceutical field is the "dry mouth syndrome" (xerostomia). The "dry mouth syndrome" causes various disorders such as feeling of thirst, xerosis of tunics mucosa oris, urtication, dysmaesesis, dyspepsia because of dryness of lip and inside the mouth due to decrease of secretion of saliva resulting from some cause. Also, the dry mouth syndrome may allow stay of food remnants inside the mouth, which may Read to dental caries.

There are various factors of causing the dry mouth syndrome. As generalized factors, the followings are known: febrile diseases, dehydration, endocrinopathy (myxedema, Basedow's disease, diabetes insipidus, etc.), dysbolism (diabetes, uremia, liver cirrhosis, etc.), deficiency of vitamin-A, B, autoimmune diseases (Sjögren's syndrome, progressive scleroderma, etc.), anemia, bleeding, aging, various medications (sedatives, parasympatholytic drugs, antihistamines, etc.). As local factors, sialadenitis, atrophy of salivary gland, sequela of radiotherapy, malformation (ectodermal dysplasia, etc.) and so forth are known.

As mentioned above, the causes of the dry mouth syndrome vary including ones which still remain unidentified. As a therapy for the dry mouth syndrome, there have been conducted several treatments such as drinking liquid all day long little by little, chewing gum or the like, and using artificial saliva. All these treatments are, however, symptomatic treatments, and providing a medicament that can establish a fundamental measures to improve decrease of saliva secretion has been strongly demanded.

Generally, a healthy person discharges 1 to 1.5 litter of saliva a day through a pair of left and right grand salivary glands (parotid gland, submandibular gland, sublingual gland) and small salivary glands (labial glands, lingual glands, palatine glands, buccal glands). Saliva is discharged in response to a stimulant that may harm a human body to dilute the same or maintain the physiological pH value thereof, as well as helping mastication and deglutition of foods. Further, saliva dissolves the food, makes a person taste the food, and helps him smoothly utter a word by keeping a wet state inside the mouth. There are two types of saliva: one is a continuous type that keeps on discharging a small amount without a particular stimulant and the other is a reflective type that is discharged in response to stimulation by food, gnatho-movement, taste of food, and the like. In any case, saliva secretion is one of essential physiological functions, and hence, improving decreased saliva secretion is particularly significant in treating the dry mouth syndrome.

DISCLOSURE OF THE INVENTION

This invention intends to solve the problems described above, and one of the objects is to provide a composition for treatment that is effective in external secretion disorders except hypolacrimation, and more particularly effective in at least one of diseases selected from hyposalivation and dry mouth syndrome.

Another object of this invention is to provide a method for treating a disease of a subject that suffers from external secretion disorders except hypolacrimation, and more particularly at least one of diseases selected from hypo salivation and dry mouth syndrome.

Still another object of this invention is to provide a use of pharmaceutical composition for treatment of external secretion disorders except hypolacrimation, and more particularly to treat at least one of diseases selected from hyposalivation and dry mouth syndrome.

The composition for treatment that solves the above problems and is effective in external secretion disorders except hypolacrimation (for instance, hyposalivation and dry mouth syndrome) has a feature that the composition comprises an aldose reductase inhibitor as an active ingredient.

The aldose reductase inhibitor may preferably comprise a compound represented by the general formula (I):

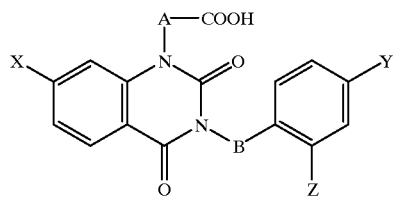

(I)

wherein

A and B are independently lower alkylene, and

X, Y, and Z are independently halogen, or a pharmacologically acceptable salt thereof. Preferably, in the general formula (I), A and B are independently methylene, X is chlorine, Y is bromine, and Z is fluorine.

The composition for treatment may preferably be in the form of preparation for oral local administration, and more preferably in the form of preparation for sublingual administration.

The method, according to another aspect of this invention, that solves the above problems and treats external secretion disorders except hypolacrimation has a feature that an aldose reductase inhibitor of an effective amount is administered to a subject in need of a treatment of external secretion disorders except hypolacrimation (for instance, hyposalivation and dry mouth syndrome).

Further, the use of pharmaceutical composition, according to still another aspect of this invention, that solves the above problems and treats external secretion disorders except hypolacrimation has a feature that an aldose reductase inhibitor is used to manufacture a pharmaceutical composition so as treat the external secretion disorders except hypolacrimation (for instance, hyposalivation and dry mouth syndrome).

BEST MODE FOR CARRYING OUT THE INVENTION

The inventors previously found and stated that a compound having an aldose reductase inhibiting-effect plays an important role in improving hypolacrimation and dry eye syndrome. Now, the inventors have also found as a further result of their researches that this compound is effective in improving external secretion disorders except hypolacrimation, particularly in improving hyposalivation and dry mouth syndrome, and come up with this invention.

The invention is explained in the following.

(1) a composition for treatment of external secretion disorders except hypolacrimation which comprises, as an active ingredient, an aldose reductase inhibitor;

(2) the composition for treatment described in (1) that is used for treatment of hyposalivation;

(3) the composition for treatment described in (1) that is used for treatment of dry mouth syndrome;

(4) the composition for treatment described in any of (1) to (3), wherein the aldose reductase inhibitor is a compound represented by the above general formula (I) (wherein A, $B_1$, X, Y, and Z are independently defined above, or a pharmacologically acceptable salt thereof;

(5) An ophthalmic composition for treatment described in (4), wherein, in the general formula (I), A and B are independently methylene, X is chlorine, Y is bromine, and Z is fluorine;

(6) The composition for treatment described in any of (1) to (5) that is in the form of preparation for oral local administration;

(7) The composition for treatment described in (6) that is in the form of preparation for sublingual administration;

(8) A method of treating external secretion disorders except hypolacrimation which comprises administering an effective amount of an aldose reductase inhibitor to an object that needs treatment for the external secretion disorders except hypolacrimation;

(9) The method described in (8) which comprises administering an effective amount of the aldose reductase inhibitor to a subject in need of a treatment of hyposalivation;

(10) The method described in (8) which comprises administering an effective amount of the aldose reductase inhibitor to a subject in need of a treatment of dry mouth syndrome;

(11) Use of an aldose reductase inhibitor in the manufacture of a pharmaceutical composition for treatment of external secretion disorders except hypolacrimation;

(12) The use of an aldose reductase inhibitor described in (11) to treat hyposalivation; and

(13) The use of an aldose reductase inhibitor described in (11) to treat dry mouth syndrome.

Hereafter, each component constituting the present invention is described.

Aldose reductase inhibitors included in this invention as the active ingredient are not specified if they can inhibit aldose reductase, being. exemplified in the concrete by the compounds represented by the above general formula (I), particularly the compound of the formula (II):

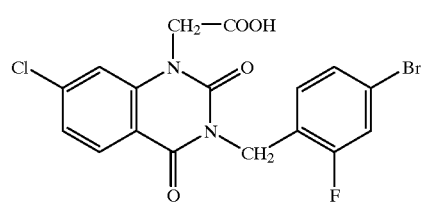

(II)

and also by epalrestat, ponalrestat, tolrestat, sorbinil, methosorbinil, imirestat, 2,3-dihydro-2,8-bis(1-methylethyl)-3-thioxo-4H-1,4-benzoxazine-4-acetic acid (AD5467), 6-fluoro-2,3-dihyro-2',5'-dioxo-(2S-cis)-spiro [4H-1-benzopyran-4,4'-imidazolidine]-2-carboxyamide (SNK-860), 8-chloro- 2',3'-dihydrospiro [pyrolizine-3,6'(5, H)-pyrolo[1,2,3-de]-[1,4]benzoxazine]2,5,5'-trion (ADN138), and 5-(3-ethoxy-4-pentyloxyphenyl)-2,4-thiazolidinedion (CT-112), etc. Particularly suitable are the compounds represented by the above general formula (I), especially the compounds shown by the above formula (II).

The terms in the general formula (I) of this specification are defined as follows:

A and B are independently lower alkylene. Lower alkylene as used in this specification mean straight or branched alkylene groups having 1 to 6 carbon atoms, preferably 1 to 4 carbon atoms. In the concrete, they are methylene, ethylene, trimethylene, propylene groups, and the like, among which methylene and ethylene groups are desirable.

X, Y, and Z are independently halogen (chlorine, bromine, fluorine, iodine), and it is particularly desirable when X is chlorine, Y is bromine, and Z is fluorine.

In this invention, the compound of the above formula (II) having methylene for each of A and B, chlorine for X, bromine for Y, and fluorine for Z in the general formula (I), i.e. [3-(4-bromo-2-fluorobenzyl)-7-chloro-2,4-dioxo-1,2,3,4-tetrahydroquinazolin-1-yl]acetate, is particularly suitable.

The compound and pharmacologically acceptable salts thereof included in this invention as the active ingredient are publicly known compounds, which can be produced for example with the method described in the Japanese Published Unexamined Patent Publication No. Sho 62-96476 or a method based on this method.

Pharmacologically acceptable salts of the compound in this invention include salts with basic compounds such as inorganic bases (e.g. sodium, potassium, calcium, magnesium, aluminum, ammonium, etc.), and organic bases (e.g. primary amines such as ethanolamine; secondary amines such as diethylamine, diethanolamine, dicyclohexylamine, N,N'-dibenzylethylenediamine, etc.; tertiary amines such as trimethylamine, triethylamine, pyridine, picoline, triethanolamine, etc.; and so on) and the like.

The aldose reductase inhibitor used in this invention is effective in treating external secretion disorders except hypolacrimation, and particularly dry mouth syndrome and improving hyposalivation in mammals including man, ox/cow, horse, dog, mouse, and rat etc., being the active ingredient in the treatment of external secretion disorders except hypolacrimation and particularly in the treatment of dry mouth syndrome and/or hyposalivation in the mammals.

The external secretion disorder except hypolacrimation in this invention means a state where an external secretion function is decreased because of some factor, e.g., Sjögren's syndrome. Some of the diseases resulting from the above external secretion disorder are: dry syndrome such as "dry mouth syndrome" (xerostomia), "dry nose syndrome" (xeromycteria), "dry skin" (xeroderma), "dry vagina syndrome" (symptom of vaginal dryness); and chronic pancreatitis, chronic gastritis, and chronic bronchitis due to depression of external secretion. Further, as the factors which may cause dry mouth syndrome, as stated above, the followings are known: febrile diseases, hypohydremia, endocrinopathy (myxedema, Basedow's disease, diabetes insipidus, etc.), cacochymia (diabetes, uremia, liver cirrhosis, etc.), deficiency of vitamin-A or B, autoimmune diseases (Sjögren's syndrome, progressive scleroderma, etc.), anemia, bleeding, aging, various medications (sedatives, parasympatholytic drugs, antihistamines, etc.), sialadenitis, atrophy of salivary gland, sequela of radiotherapy, malformation (ectodermal dysplasia, etc.) and so forth. Saliva secretion disorder in this specification means an anomalous state (depression or suppression) of saliva secretion caused by some factor.

Treatment with the composition for treatment of this invention includes all controls, including prevention, cure, relief or decrement of symptom, suppression of progress, etc.

The composition for treatment of this invention may be administered orally or parenterally, but local administration (for instance, mouth) onto parts required is particularly desirable when the avoidance of the influence on other areas of the cardiovascular system and the significance of their actual effectiveness, etc. are taken into account.

For instance, sublingual tablets, troches, chewable tablets, collutoriums, sprays, ointments, powders, granules, tablets, capsules, injections, ophthalmic solutions are some of the forms for preparations, and preferably, the form of sublingual tablet, troches, sprays and ointments is suitable. These preparations can be manufactured according to known art.

In addition, ingredients having pharmacological activity different from that of the ingredient of this invention may be added as needed to the pharmaceutical preparations of this invention if they are compatible to the purpose of the invention.

The dose and dosing frequency of the active ingredient of this invention vary according to the symptoms of the disease to be treated, age and body weight of the patient, dosage form, treatment duration, therapeutic effect desired, etc. In general, in case of use as a sublingual tablet of the preparation containing 0.001 to 10.0 w/v%, preferably 0.01 to 1.0 w/v%, of an aldose reductase inhibitor, oral dosage of several times, preferably 1 to 6 times a day brings about a satisfactory effect for an adult. Likewise, in case of use as an ointment of the preparation containing 0.001 to 10.0 w/v%, preferably 0.01 to 1.0 w/v%, of an aldose reductase inhibitor, application of the ointment several times, preferably 1 to 6 times a day onto the parts of the body required, brings about a satisfactory effect for an adult.

In this invention, one active ingredient alone or two or more active ingredients in combination may be contained in the preparation. In the preparation that contains two or more active ingredients, the amount of each ingredient may be determined appropriately according to the therapeutic effect and safety of each ingredient.

This invention is explained in the concrete in the Example described below, and the invention is not limited at all by the Example.

EXPERIMENTAL EXAMPLE 1

[3-(4-Bromo-2-fluorobenzyl)-7-chloro-2,4-dioxo-1,2,3,4-tetrahydroquinazolin-1-yl]acetate, a compound represented by the general formula (II) having aldose reductase-inhibiting effect as an active ingredient was used for preparation of a 0.3% eye drops.

The 0.3% eye drops was instilled to a diabetic patient (female, 43 years old) four times a day. On the sixth day after the administration has started, an obvious sthenia of saliva secretion of the patient was observed.

As seen from the experiment, it was verified that the aldose reductase inhibitor is effective in improvement of hyposalivation or dry mouth syndrome.

EXPERIMENTAL EXAMPLE 2

[3-(4-Bromo-2-fluorobenzyl)-7-chloro-2,4-dioxo-1,2,3,4-tetrahydroquinazolin-1-yl]acetate, a compound represented by the general formula (II) having aldose reductase-inhibiting effect as an active ingredient was used for preparation of a 0.3% solution.

Male Sprague-Dawley rats (aged 7 weeks) were used. The rats were intraorally administered with 50 $\mu$L of the 0.3% solution or distilled water three times a day (10:00, 14:00, 18:00) on Day 1 and Day 2. On Day 3, the time upon lapse of one hour after the administration at 10:00 and 14:00, a strip of filter-paper (Schirmer Tear Production Measuring Strips: SHOWA YAKUHIN KAKO CO., LTD.) with the length of 37 mm and width of 5 mm was inserted between the lower teeth gums and the lower jaw of the rat to absorb the saliva into the filter-paper. The infiltration distance of the saliva into the filter-paper was measured every 1 minute for 5 minutes. The result is shown in Table 1.

TABLE 1

Effect on saliva secretion in rats

| Group | No. of Rats | The infiltration distance of the saliva into filter-paper, mm, mean ± S.E. | | | | |
|---|---|---|---|---|---|---|
| | | after 1 min. | after 2 min. | after 3 min. | after 4 min. | after 5 min. |
| Control group (supplied with Distilled Water) | 8 | 5.5 ± 0.4 | 6.9 ± 0.5 | 7.8 ± 0.8 | 8.5 ± 0.7 | 9.3 ± 0.8 |
| Test group | 8 | 8.1 ± 1.5 | 10.6 ± 1.8 | 12.6 ± 2.0* | 13.6 ± 2.1* | 14.5 ± 2.3 |

* P<0.05, comparison with control group (according to Mann-Whitney U-test)

As seen from the experiment, it was verified that the aldose reductase inhibitor is effective in improvement of hyposalivation or dry mouth syndrome, since the aldose reductase inhibitor has a significant effect on increasing of saliva secretion.

INDUSTRIAL APPLICABILITY

The composition for treatment of this invention including an aldose reductase inhibitor as an active ingredient is effective in improvement of external secretion disorders except hypolacrimation, particularly hyposalivation and dry mouth syndrome. Therefore, the composition for treatment of this invention is suggested to be useful for treatment of external secretion disorders except hypolacrimation.

What is claimed is:

1. A method for treating an exocrine disorder except hypolacrimation which comprises administering an effective amount of an aldose reductase inhibitor to a subject in need of a treatment of said exocrine disorder except hypolacrimation.

2. The method of claim 1 wherein the exocrine disorder is hyposalivation.

3. The method of claim 1 wherein the exocrine disorder is dry mouth syndrome.

4. The method of claim 1, wherein the aldose reductase inhibitor is a compound represented by the formula (I):

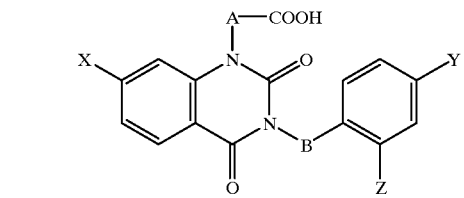

wherein

A and B are independently lower alkylene,

X, Y, and Z are independently halogen, or a pharmacologically acceptable salt thereof.

5. The method of claim 4, wherein A and B are independently methylene, X is chlorine, Y is bromine, and Z is fluorine.

6. The method of claim 1 in which the aldose reductase inhibitor is administered locally in the form of a preparation for local administration to the oral cavity.

7. The method of claim 6 in which the aldose reductase inhibitor is administered locally in the form of a preparation for sublingual administration.

* * * * *

UNITED STATES PATENT AND TRADEMARK OFFICE
CERTIFICATE OF CORRECTION

PATENT NO. : 6,339,088 B1
DATED : January 15, 2002
INVENTOR(S) : Ryuji Ueno and Ichie Kato It is certified that error appears in the above-identified patent and that said Letters Patent is hereby corrected as shown below:

Column 1,
Line 5, delete "Feb. 13, 2000" and insert -- Feb. 15, 2000 --.

Signed and Sealed this

Twenty-third Day of April, 2002

Attest:

JAMES E. ROGAN
*Attesting Officer*     *Director of the United States Patent and Trademark Office*